United States Patent
Humboldt

[11] Patent Number: 5,927,972
[45] Date of Patent: Jul. 27, 1999

[54] CROWN CEMENTATION SEATING

[76] Inventor: Geoff Humboldt, 4343 Grand Ave., Suite 105, Gurnee, Ill. 60031

[21] Appl. No.: 08/898,259

[22] Filed: Jul. 22, 1997

[51] Int. Cl.$^6$ ........................................................ A61C 5/08
[52] U.S. Cl. .............................. 433/25; 433/218; 433/226; 433/141
[58] Field of Search ...................... 433/218, 223, 433/226, 141, 136, 138, 140, 149, 155

[56] References Cited

U.S. PATENT DOCUMENTS

| | | |
|---|---|---|
| 2,183,624 | 12/1939 | Schwartz . |
| 2,624,942 | 1/1953 | Wilborn .................................. 433/150 |
| 2,937,446 | 5/1960 | Weisenfeld . |
| 3,722,101 | 3/1973 | Via, Jr. . |
| 3,874,084 | 4/1975 | Cole ....................................... 433/141 |
| 3,903,606 | 9/1975 | Oliver . |
| 3,974,567 | 8/1976 | Ridgeway . |
| 4,063,552 | 12/1977 | Going et al. . |
| 4,219,619 | 8/1980 | Zarow . |
| 4,259,070 | 3/1981 | Soelberg et al. ......................... 433/149 |
| 4,541,803 | 9/1985 | Adler . |
| 4,773,857 | 9/1988 | Herrin . |
| 4,828,494 | 5/1989 | Angus et al. . |
| 4,919,615 | 4/1990 | Croll . |
| 4,975,053 | 12/1990 | Hofsess . |
| 4,983,122 | 1/1991 | Mitnick . |
| 5,030,098 | 7/1991 | Branford . |
| 5,090,903 | 2/1992 | Taylor et al. . |
| 5,261,817 | 11/1993 | Nack ....................................... 433/141 |
| 5,299,936 | 4/1994 | Ueno . |
| 5,320,533 | 6/1994 | Lee . |
| 5,513,984 | 5/1996 | Ueno . |
| 5,525,059 | 6/1996 | Lee . |
| 5,527,181 | 6/1996 | Rawls et al. ......................... 433/136 X |
| 5,575,649 | 11/1996 | Lee . |

FOREIGN PATENT DOCUMENTS

| | | |
|---|---|---|
| 83100984 | 2/1983 | European Pat. Off. . |
| 340485 | 5/1936 | Italy ....................................... 433/149 |

*Primary Examiner*—Nicholas D. Lucchesi
*Attorney, Agent, or Firm*—McDonnell Boehnen Hulbert & Berghoff

[57] ABSTRACT

A crown cementation seating comprising a longitudinal portion having opposed first and second ends and a central portion therebetween. The central portion having a width that corresponds generally to the central groove of the crown and that is less than the distance between the lingual and buccal cusps of the crown.

18 Claims, 2 Drawing Sheets

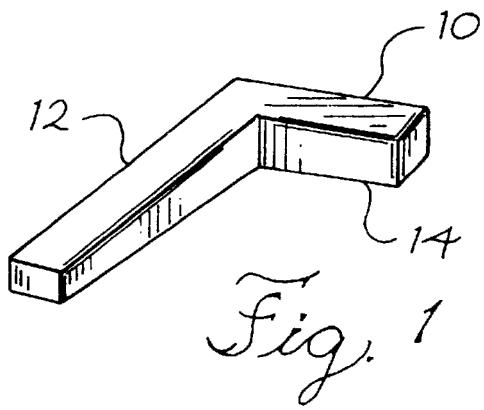
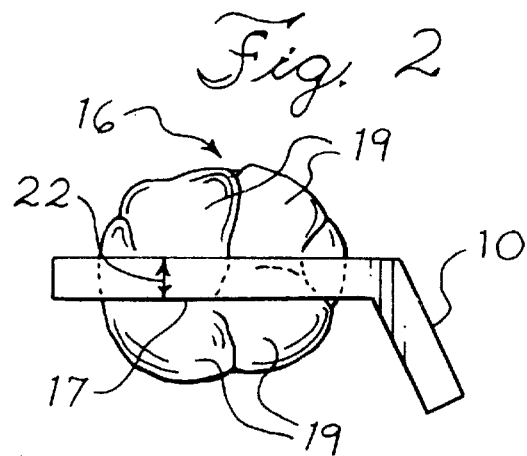
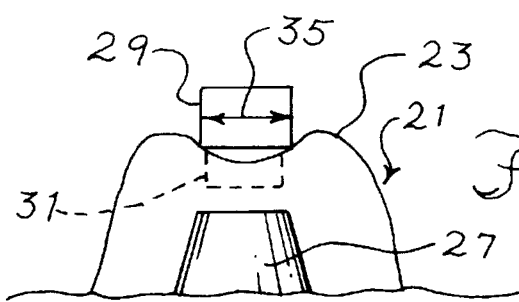
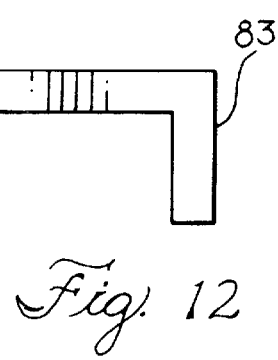
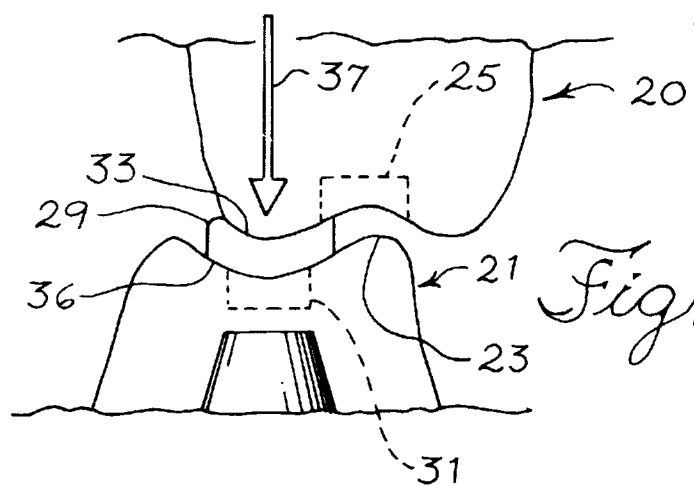
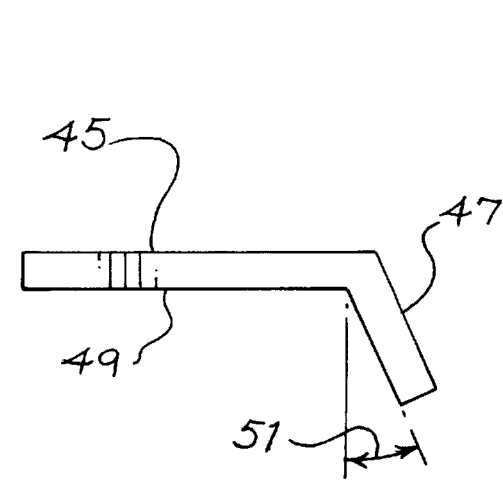
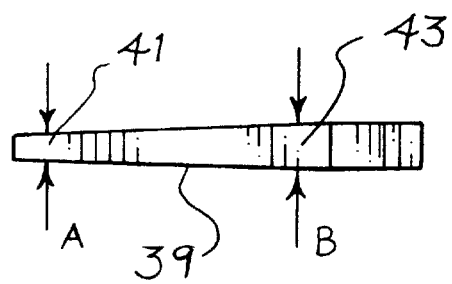

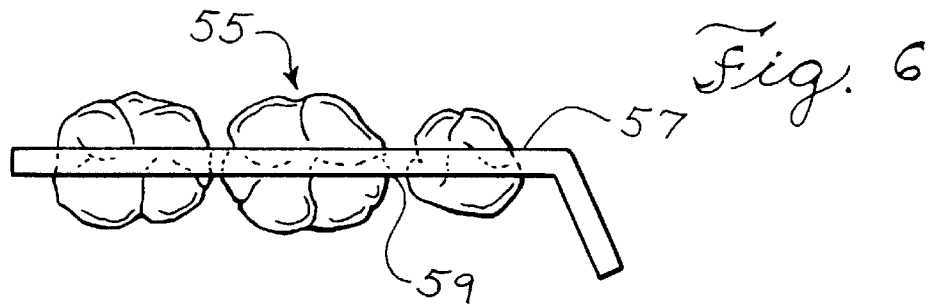
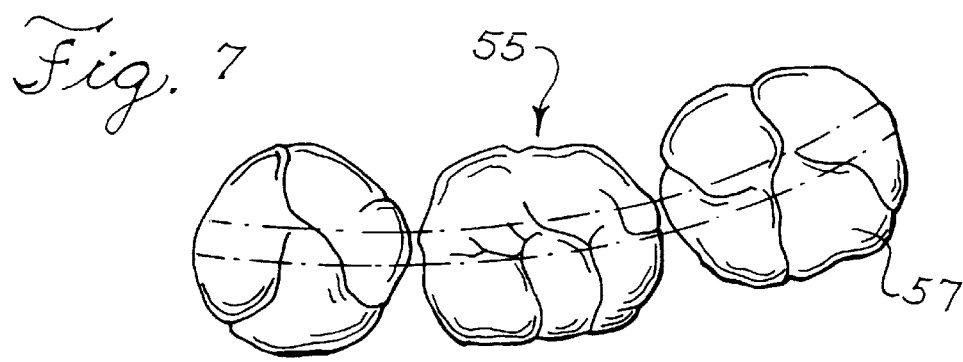
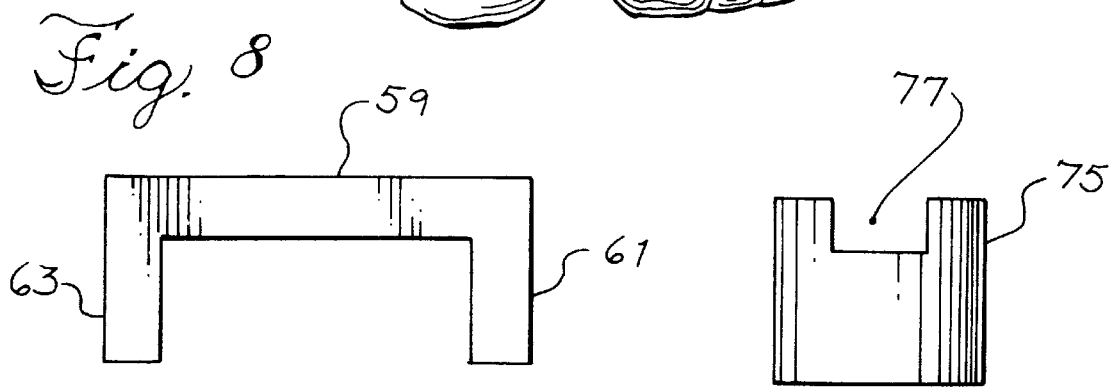
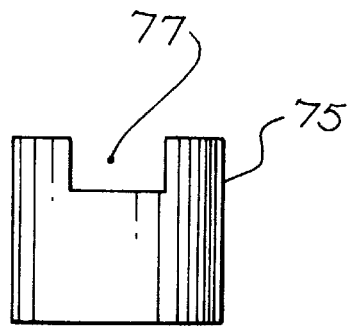
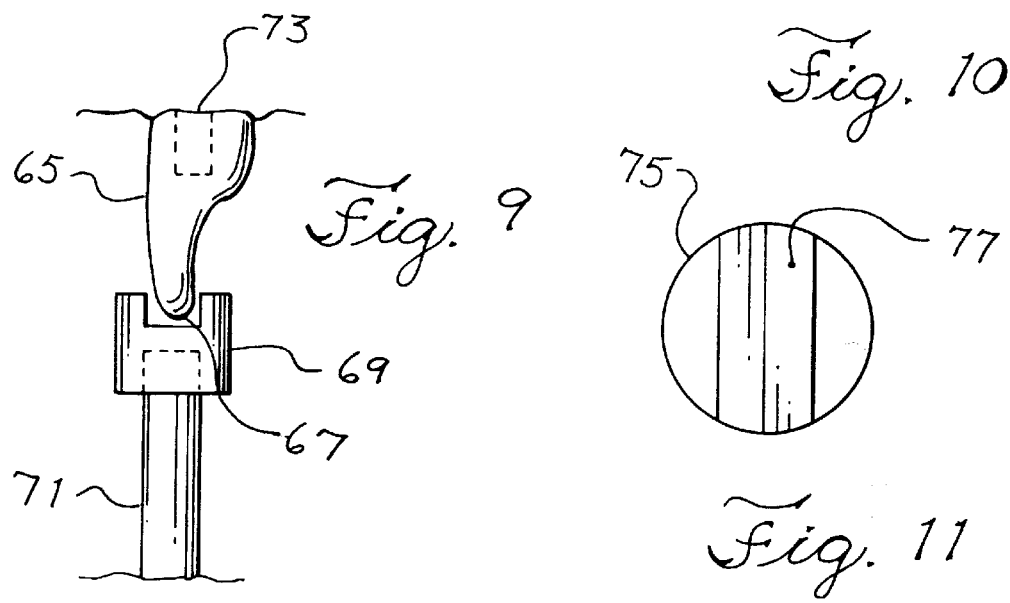
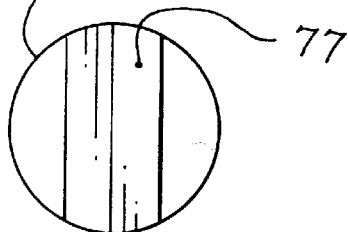

CROWN CEMENTATION SEATING

FIELD OF THE INVENTION

This invention pertains to the seating of crowns, bridges, onlays, inlays, and other dental restorative elements, and more particularly to a device to facilitate the proper and complete cementation seating of such crowns, bridges, and other dental restorative elements.

BACKGROUND OF THE INVENTION

For years, artificial restorative elements such as crowns, bridges, onlays, and inlays have been used in the field of dentistry. A crown is a single artificial tooth replica typically made of porcelain, or cast metal, or porcelain bonded to cast metal that is designed to fit over a tooth that has often been ground into the form of a stump. The crown has a similar configuration as the original tooth and is used as a restorative element. A bridge is composed of multiple crowns with artificial teeth interposed therebetween. In addition, onlays and inlays, or partial crowns, are used to restore portions of a tooth. For purposes of this application, the term "crown" will be used to represent all of the various types of crowns and bridges and onlays. The crown is bonded to the stump of the tooth using dental cement such as zinc phosphate cement or other bonding cements.

To ensure the longevity of the crown, it is very important that the crown is properly seated onto the tooth. Also, an improperly seated crown can compromise the marginal integrity of the crown. Decay can develop underneath the crown and the occlusion or bite may be off slightly causing the grinding down of the crown. Typically, the crown is placed over the tooth and the patient applies biting pressure on an object to force the crown into place. The biting pressure is applied while the dental cement hardens and a bond between the crown and tooth is formed. In the prior art, patients have applied biting pressure to an orangewood stick during the cementation of the crown. However, it has been found that the use of an orangewood stick may result in the cracking or chipping of the porcelain crown, necessitating the time and expense of manufacturing and reseating a new crown. Furthermore, the load applied to the crown with the use of the orangewood stick is uneven and can result in a crown that is improperly seated. Other prior art techniques include applying biting pressure to a rubber bite block such as that shown in U.S. Pat. No. 4,975,053 where the biting pressure is applied across the entire width of the tooth to be crowned. However, these prior art devices have similar shortcomings as discussed below, in that they fail to provide a device that allows for the uniform loading of the central groove of the tooth to be crowned, without also loading the lingual or buccal cusps of the crown.

SUMMARY OF THE INVENTION

The present invention is directed to a crown cementation seating device that provides for biting pressure to be applied to the central groove of the tooth to be crowned. It is very important to properly seat a crown during the cementation process. An improperly seated crown will result in a weakened bond between the tooth and crown and significantly diminish the useful life of the crown. Also, an improperly seated crown may result in decay forming underneath the crown and may adversely affect the occlusion or bite.

The present invention is specifically directed to an elastomeric cementation seating that is adapted to transmit biting pressure only through the central groove of the tooth to be crowned. The central groove is defined as the centerline of the occlusal surface or biting surface of the teeth. The central groove extends generally from the back or distal portion of the tooth to the front or mesial portion of tooth, generally along the centerline of the tooth. Taking the bottom molars as an example, the central groove of the bottom molars is the region at which the inner or lingual cusp(s) of the upper mating molar(s) contact the bottom molar(s) during biting and corresponds generally to the back to front (distal to mesial) centerline of the bottom molar(s). Similarly, the central groove of the upper molar(s) is the region at which the outer or buccal cusp(s) of the mating bottom molar(s) contact the upper molar(s) during biting and generally corresponds to the back to front (distal to mesial) centerline of the upper molar(s).

With respect to the crowning of a bottom molar, the crown cementation seating of the present invention contemplates the application of biting pressure to be transmitted axially (perpendicular to the biting surface) from the inner or lingual cusp(s) of the mating upper molar through the elastomeric cementation seating to the central groove of the bottom molar to be crowned, without the application of biting pressure transmitted from the central groove of the upper mating molar through the elastomeric cementation to the outer or buccal cusp(s) of the bottom molar to be crowned. Importantly, it has been found that when biting pressure is applied to both the central groove of the molar to be crowned as well as the outer or buccal cusp(s) of the molar to be crowned, an undesirable moment of force is applied through the buccal cusp(s) of the molar to be crowned which causes non-uniform loading and improper seating of the crown. With the cementation seating of the present invention, biting pressure is only applied to the central groove of the molar to be crowned. There is no moment of force applied through the buccal cusp(s) of the bottom molar and the application of biting pressure is directed axially through the central groove of the bottom molar. To accomplish the axial loading of the central groove only, the crown cementation seating of the present invention has a width that is less than the width of the occlusal or biting surface of the bottom molar such that the cementation seating does not allow for biting pressure to be transmitted from the central groove of the upper mating molar through the outer or buccal cusp(s) of the bottom molar.

When a seating having a width equal to or greater than the width of the occlusal or biting surface of the tooth to be crowned is used, an undesirable moment of force is caused by the transmission of biting pressure from the central groove of the mating tooth through the cusps of the tooth to be crowned. This undesirable moment of force does not allow for only the axial loading of the central groove of the tooth to be crowned and can result in an improperly seated crown. By employing the reduced width cementation seating of the present invention such undesirable moment of force is eliminated.

In an additional embodiment, a crown cementation seating for the incisors (or front teeth) is provided. Unlike the molars, there is no mating or biting surface between the upper and lower incisors. To seat the crown of an incisor, the dentist typically presses the crown into place using his fingers or thumb to partially seat the crown. To complete the seating, an implement such as an orangewood stick is tapped against the incisal or biting edge of the crown to fully seat it. However, the use of an orangewood stick does not provide a uniform force to be applied across the incisal edge and may result in a hairline fracture or cracking of the crown.

In the present invention, an elastomeric cementation seating is provided that is designed fit over an end of an orangewood stick or other device suitable for use with a tapping mallet. The end of the orangewood stick with the crown cementation seating affixed thereto is placed against the incisal edge of the crown. A tapping mallet is used to transmit a force axially through the orangewood stick to fully seat the crown. Since the cementation seating is made of a deformable elastomeric material, the seating force is uniformly applied over the incisal edge. In this manner, the crown cementation seating facilitates the proper seating of the crown and helps to prevent cracks or fractures that may result where only an orangewood stick is used. The crown cementation seating may include a centrally located slot to be placed over the incisal edge of the crown to facilitate proper alignment of the cementation seating and crown.

BRIEF DESCRIPTION OF THE DRAWINGS

FIG. 1 is a perspective view of a crown cementation seating.

FIG. 2 is a top view of a crown cementation placed along the central groove of the occlusal or biting surface of teeth.

FIG. 3 is a plan view of a crown cementation seating placed along the central groove of a bottom molar.

FIG. 3A is a plan view of a crown cementation seating placed along the central groove of a bottom molar during the application of biting pressure from a mating upper molar.

FIG. 4 is a side view of a crown cementation seating.

FIG. 5 is a top view of a crown cementation seating.

FIG. 6 is a top view of a crown cementation seating used in connection with a bridge.

FIG. 7 depicts a top view showing the central groove of a row of teeth.

FIG. 8 depicts a crown cementation having two outwardly extending tangs.

FIG. 9 depicts a crown cementation seating for use with the incisor teeth.

FIG. 10 is a side view of a crown cementation seating for use with the incisor teeth.

FIG. 11 is a top view of a crown cementation seating for use with the incisor teeth.

FIG. 12 depicts a crown cementation seating having two outwardly extending tangs.

DETAILED DESCRIPTION OF THE PREFERRED EMBODIMENT OF THE INVENTION

A crown cementation seating 10 is shown in FIG. 1. The longitudinal portion 12 is shown that will be placed along the central groove of the tooth to be crowned during cementation seating. Angularly extending tang 14 extends from the longitudinal portion 12 to allow for the cementation seating to be gripped by a forceps or other tool by the dentist during placement and removal of the cementation seating. The crown cementation seating is preferably made from an elastomeric material having the ability to compress moderately during biting pressure. The material should be moderately rigid, but sufficiently resilient so that the material will compress during the application of biting pressure. One possible material is a copolymer of ethylene and vinyl acetate containing 12% vinyl acetate.

The longitudinal portion is approximately 0.125 inches thick and the width is approximately 0.125 in width, to generally correspond to the central groove of the tooth. FIG. 2 shows a top view of the cementation seating placed over crown 16 along the central groove of the crown. The central portion 17 is placed over the central groove and has a reduced width dimension 22 that is out of contact with the cusps 19 when placed along the central groove of crown 16.

FIG. 3 shows the crown 21 placed over the stump 27 of a bottom molar. The longitudinal portion 29 of the crown cementation seating is placed along the central groove 31 (shown in dotted lines) of the crown 21. FIG. 3A depicts the crown cementation seating 29 during the application of biting pressure from upper mating molar 20. The longitudinal portion 29 is compressed during the application of biting pressure. The inner or lingual cusps 33 of mating upper molar 20 is shown transmitting an axial force 37 through the longitudinal portion 29 of the crown cementation seating to the central groove 31 of the crown 21. As seen in FIG. 3A, the central groove 25 (shown in dotted lines) of the mating upper molar 20 does not apply biting pressure through the longitudinal portion 29 of the cementation seating to the outer or buccal cusps 23 of the crown 21. There is no transmission of force through the central groove 25 of the upper mating molar 20 through the longitudinal portion 29 to the outer or buccal cusps 23 of crown 21.

As a result, there is no undesirable moment of force created about the outer or buccal cusps 23 of crown 21. Instead, because the width 35 of the longitudinal portion 29 is less that the width of the occlusal or biting surface 36, only an axial force directed through the central groove of the crown 21 is transmitted from upper mating molar 20 during the application of biting pressure. This aspect of the invention is significant in that the force from the biting pressures applied by upper mating molar 20 only applies a force 37 axially through the central groove 31 of the crown 21. No force is applied to the outer or buccal cusps 23 of crown 21. Consequently, the crown cementation seating facilitates the proper seating of the crown by transmitting an axial force through the central groove of the crown without also having an undesirable moment created by having a force transmitted to the outer or buccal cusps 23 of the crown 21.

FIG. 4 shows a crown cementation seating having a tapered longitudinal portion 39 having a thickness dimension 41 at the posterior end that is less than the thickness dimension 43 at the anterior end. The thickness dimension 43 at the longitudinal end is approximately 0.125 inches. The tapered longitudinal section is designed to accommodate for the geometry of the jawline during biting. The upper and lower molars are closer together at the posterior of the mouth than at the anterior. The tapered longitudinal portion 39 shown in FIG. 4 accommodates this geometry of the jawline. Preferably, the taper of the longitudinal portion will be approximately 15 degrees.

FIG. 5 show a crown cementation seating 45 having an angularly extending tang 47 that extends from the longitudinal portion 49. The angle 51 may be approximately 45 degrees and allows the angularly extending tang 47 to extend towards the anterior of the mouth to facilitate gripping of the cementation seating during placement and removal.

FIG. 6 shows a crown cementation seating used in connection with a bridge 55. The longitudinal portion 59 of the cementation seating is placed generally along the centerline or central groove 57 of the bridge. The dotted lines of FIG. 7 depict the central groove 57 of the bridge 55.

FIG. 8 depicts a crown cementation seating 59 having two outwardly extending tangs 61 and 63. Forward tang 61 may used to place the cementation in the mouth while tang 63 acts as a gauge to determine the alignment and placement of the cementation seating.

FIG. 9 depicts incisor crown 65 placed over the tooth stump 73. Crown cementation seating 69 is affixed to orangewood stick 71 to transmit a force to the incisal edge 67 of the crown 65 to seat the crown. FIG. 10 depicts a side view of crown cementation seating 75 having a slot 77 to receive the incisal edge of the crown. FIG. 11 is a top view of crown cementation seating 75 and showing a slot 77 to receive the incisal edge of the crown.

With respect to FIG. 9, a crown cementation seating for use with the incisor or front teeth is shown. The dentist initially places the crown 65 over the incisor stump 73. To complete the seating, crown cementation seating 69 is placed over an implement such as an orangewood stick 71. Using a mallet or other similar device, the dentist taps the orangewood stick to transmit a force axially through the orangewood stick 71 and affixed crown cementation seating 69 to the incisal edge 67 of the crown 65. Since the cementation seating 69 is made of a deformable elastomeric material, the seating force is uniformly applied over the incisal edge. As a result, the crown cementation seating facilitates the proper seating of the crown and helps to prevent cracks or fractures that may result where only an orangewood stick is used.

As shown in FIGS. 10 and 11, the crown cementation seating 75 may include a centrally located slot 77 that corresponds to the incisal edge of the crown to facilitate proper alignment of the cementation seating and crown during seating.

FIG. 12 discloses an alternative embodiment wherein the cementation seating includes a first tang 81 outwardly extending at an angle of approximately 45 degrees and a second tang 83 outwardly extending at an angle of ninety degrees Whereas the invention has been shown and described in connection with the preferred embodiments thereof, it will be understood that modifications may be made which are within the intended scope of the appended claims.

I claim:

1. A cementation seating for use in the seating and cementation of a dental crown having one or more lingual or buccal cusps, comprising:

a longitudinal portion of resilient and deformable elastomeric material having opposed first and second ends and a central portion therebetween, said central portion having a width that corresponds generally to a central groove of the crown and that is less than a distance between the lingual and buccal cusps of the crown, such that when the central portion of the crown cementation seating is placed along the central groove of the crown there is no contact between said cementation seating and either the lingual or buccal cusps of the crown; said central portion having a length that is greater than a mesial to distal length of the crown;

and a tang outwardly extending from said longitudinal portion.

2. The cementation seating of claim 1 wherein the central portion of said cementation seating is tapered such that the central portion has a thickness dimension at said first end that is greater than a thickness dimension at said second end.

3. The cementation seating of claim 2 wherein the central portion of said cementation seating is tapered at approximately a fifteen degree angle.

4. The cementation seating of claim 1 wherein the central portion of said cementation seating has a thickness dimension that is less than or equal to the width of said central portion.

5. The cementation seating of claim 1 wherein the width of said central portion is approximately 0.125 inches.

6. The cementation seating of claim 1 wherein said central portion has a thickness dimension of approximately 0.125 inches.

7. The cementation seating of claim 1 wherein said tang outwardly extends from said first end of said longitudinal portion.

8. The cementation seating of claim 7 further including a second tang outwardly extending from said central portion.

9. The cementation seating of claim 8 wherein the tang outwardly extends from said longitudinal portion at an angle of approximately 45 degrees, and said second tang outwardly extends at a ninety degree angle from said second end.

10. The cementation seating of claim 1 wherein during the application of biting pressure to the crown from a mating molar having a central groove, no force is transmitted from the central groove of the mating molar through said cementation seating to either the lingual or buccal cusps of the crown.

11. A cementation seating for use in the seating and cementation of a dental crown having one or more lingual or buccal cusps, comprising:

a longitudinal portion of resilient and deformable material having opposed first and second ends and a central portion therebetween, said central portion having a width that corresponds generally to a central groove of the crown and that is less than a distance between the lingual and buccal cusps of the crown, such that when the central portion of the crown cementation seating is place along the central groove of the crown there is no contact between said cementation seating and either the lingual or buccal cusps of the crown; said central portion having a length that is greater than a mesial to distal length of the crown; and wherein the central portion of said cementation seating is tapered such that the central portion has a thickness dimension at said first end that is greater than a thickness dimension at said second end; and wherein the thickness dimensions of said central portion of said cementation seating are less than or equal to the width of said central portion;

and a tang outwardly extending from said longitudinal portion.

12. The cementation seating of claim 11 wherein the width of said central portion is approximately 0.125 inches.

13. A cementation seating for seating and cementation of an incisor crown having an incisal edge comprising:

A resilient and deformable elastomeric material having oppositely disposed first and second sides; said first side having a seating surface to contact the incisal edge of the crown and said second side having sides defining an opening; said opening adapted to receive a force transmission device, wherein a force may be transferred from the force transmission device through the cementation seating to the crown.

14. The cementation seating of claim 13 wherein said seating surface includes a slot corresponding to the incisal edge of the crown to be seated.

15. The cementation seating of claim 14 wherein said slot has a width substantially equal to the width the incisal edge of the crown.

16. The cementation seating of claim 13 wherein said force transmission device comprises an orangewood stick.

17. The cementation seating of claim 13 wherein said seating surface has a width greater than the surface of the incisal edge of the crown.

18. The cementation seating of claim 13 wherein said elastomeric material is sufficiently deformable to apply a uniform load to the incisal edge during seating.

* * * * *